(12) United States Patent
Chihani et al.

(10) Patent No.: US 6,878,857 B1
(45) Date of Patent: Apr. 12, 2005

(54) FIBROUS STRUCTURE AND ABSORBENT ARTICLE INCLUDING SUCH A FIBROUS STRUCTURE

(75) Inventors: Thami Chihani, Mölnlycke (SE); Panayotis Cocolios, Bullion (FR); François Coeuret, Guyancourt (FR); Anna Nihlstrand, Göteborg (SE); Alain Villermet, Viroflay (FR)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/744,920
(22) PCT Filed: Aug. 2, 1999
(86) PCT No.: PCT/EP99/05580
§ 371 (c)(1), (2), (4) Date: Jan. 31, 2001
(87) PCT Pub. No.: WO00/08248
PCT Pub. Date: Feb. 17, 2000

(30) Foreign Application Priority Data

Aug. 6, 1998 (EP) .............................................. 98402010

(51) Int. Cl.⁷ ............................ A61F 13/15; A61F 13/20
(52) U.S. Cl. .......................... 604/365; 604/367; 604/375
(58) Field of Search ................................ 604/365, 367, 604/375, 378, 373; 427/446, 452, 527, 501

(56) References Cited

U.S. PATENT DOCUMENTS

| 3,738,626 A | 6/1973 | Norback |
| 3,862,280 A | 1/1975 | Polovina |
| 4,296,050 A | 10/1981 | Meier |
| 4,459,244 A | 7/1984 | Norback |
| 4,668,443 A | 5/1987 | Rye |
| 5,540,672 A | * 7/1996 | Roessler et al. ........ 604/385.26 |
| 5,576,076 A | 11/1996 | Slootman et al. |

FOREIGN PATENT DOCUMENTS

| EP | 0 311 989 | 10/1988 |
| EP | 0 483 859 | 10/1991 |
| EP | 0 524 529 | 7/1992 |
| JP | 11 92871 | 8/1989 |
| JP | 51 56055 | 6/1993 |
| WO | WO 92/03591 | 3/1992 |
| WO | WO 99/05358 A1 | 2/1999 |

OTHER PUBLICATIONS

Sarmadi et al, "Improved Dyeing Properties of $SiCi_4$ (ST)–Plasma Treated Polyester Fabrics", *Textile Chemist and Colorist*, vol. 28, No. 6, Jun. 1, 1996, pp. 17–22; Search Report issued in International Application No. PCT/EP99/05580.

* cited by examiner

*Primary Examiner*—Larry I. Schwartz
*Assistant Examiner*—Michele Kidwell
(74) *Attorney, Agent, or Firm*—Burns, Doane, Swecker & Mathis, L.L.P.

(57) ABSTRACT

A fibrous structure is described for use in hygienic articles such as diapers, sanitary napkins, incontinence guards, wipes and the like, having one or more polar, silicon containing compounds bound to at least one portion of the surface of the fibrous structure by interaction between the surface and the silicon containing compounds. The fibrous structure exhibits a predetermined degree of hydrophilicity and adhesion properties which are substantially unaffected by wetting of the fibrous structure. Absorbent, hygienic and textile articles comprising such a fibrous structure are also described.

35 Claims, 2 Drawing Sheets

FIBROUS STRUCTURE AND ABSORBENT ARTICLE INCLUDING SUCH A FIBROUS STRUCTURE

BACKGROUND OF THE INVENTION

1. Field of the Invention

The present invention relates to a fibrous structure (either of the woven or non-woven type, natural or synthetic etc.). As it is well known, such fibrous structures are used in many industrial applications, such as those given hereafter by way of illustration without any limitation:

- hygienic articles (feminine as well as medical/surgical) such as diapers, sanitary napkins, incontinence guards, wipes, wound dressing, face masks and the like;
- industrial applications such as for use in isolation products (thermal, electrical) or filtration products, or else floor coverings;
- textile products.

2. Description of Related Art

Depending on the kind of fibrous structures and applications considered, properties of hydrophilicity and/or adhesion will be particularly looked for.

Taking the example of non-woven materials, they are produced from comparatively hydrophobic synthetic fibres such as, for example, fibres of polypropylene or polyethylene which are treated and/or apertured in order to make the materials liquid permeable.

In order to obtain fluid absorbent articles which exhibit good wicking ability, a high total and local fluid uptake capacity, good fluid retaining capacity and a high degree of surface dryness, such articles are usually built up of a plurality of different non-woven fibrous structures having different functions. One major problem when constructing fluid absorbent articles of this kind is, however, that it is difficult to obtain optimal wettability i.e. an optimal degree of hydrophilicity which remains unchanged after the article has been exposed to wetting. Furthermore, it is difficult to obtain stable wetting characteristics in absorbent articles which are stored for an extended period of time.

In WO 91/05108, it has been experimentally shown that there is a connection between increased surface area and increased rate of absorption. The patent application relates to fibres which have been provided with a porous layer attached to the surface of the fibres. The porous layer increases the specific surface of the fibres which implies that absorbent material containing such fibres obtains an improved rate of absorption and wicking ability.

The porous layer is created by impregnating fibrous material with hydrophilic chemicals while the fibres are kept in a dry or in a wet state in the form of dewatered fibre pulp or in the form of an aqueous suspension of fibres, respectively. The treatment may be performed by bringing the fibres into contact with the hydrophilic chemicals for instance by spraying fibres in a formed absorbent layer with a chemical solution or by mixing the chemicals with a fibre suspension wherein the chemicals are added as solids, in a solution, or in any commercially available form.

Regarding fluid permeable cover sheets for use in absorbent articles such as diapers, incontinence guards and sanitary napkins, wherein the cover sheet is intended to be in contact with the body of a user during use, it is important that the cover sheet could stand repeated wettings.

In other words, the cover sheet should remain fluid permeable even after the absorbent article has been exposed to fluid impact several times. Furthermore, it is important that the cover sheet can accept a large amount of fluid during a short interval of time. Another important property of the fluid permeable cover sheet is the ability to exhibit high surface dryness even after having been exposed to several wettings. In order to obtain a cover sheet having the desired properties, it is important that the cover sheet exhibits an optimal, i.e. a desired, degree of hydrophilicity and that the degree of hydrophilicity varies only within a very limited range when the fibrous structure is wetted or when it is subjected to ageing.

As well known to the man skilled in the art, the literature of these fields talk about the properties of "hydrophilicity" or "wettability" of a substrate, or else of "adhesion" of a third body on a substrate and often report measurements of "surface tension", "contact angle" and "peeling test" to evaluate such properties.

A commonly used method for increasing the wettability of fluid permeable cover sheets for use as cover sheets in absorbent articles, is to treat the material with surfactants. Non-woven materials used as cover sheets for absorbent articles are usually made of synthetic materials which are inherently hydrophobic and which have been treated with surfactants in order to become wettable and readily permeable to fluids. The treatment is usually carried out by coating the hydrophobic material with a surfactant. In order for a material to be fluid wettable, the contact angle between the surface of the material and the fluid must be less than 90°. However, a problem in connection with using cover sheets which have been coated with a surfactant is that such cover sheets exhibit decreasing fluid permeability with repeated wetting. The reason for this is that the applied surfactants are not firmly attached to the surface of the cover material and will be detached from the cover material and solved in body fluid during the first wetting. At subsequent wettings the amount of surfactant which remains on the surface of the cover sheet is therefore considerably reduced, resulting in impaired fluid permeability.

Another problem in relation to the use of articles having surfactant-coated cover sheets is that the surfactant compounds may migrate from the cover sheet to the skin of the user, thereby causing skin irritation.

An additional problem with absorbent articles having cover sheets of this kind is that during storage of the article the surfactants may migrate from the cover sheet into the absorbent structure, resulting in the fluid permeability of the cover sheet being insufficient even at the first fluid impact.

Still another problem with surfactant-coated cover sheets is that the method of applying the surfactant is less attractive from an environmental point of view since the surfactant agent is usually applied to the surface of the material in the form of a solution which, for instance, is sprayed over the surface and causes the surfactant to be emitted into the ambient air.

The present invention provides a fibrous structure of the kind mentioned in the introduction. The fibrous structure exhibits when desired a well defined rate of wetting, i.e. a predetermined degree of hydrophilicity which is substantially unaffected by wetting of the fibrous structure, and/or good properties of adhesion which are substantially unaffected by wetting of the fibrous structure.

Furthermore, with the present invention a fibrous structure is provided, wherein the desired, predetermined degree of hydrophilicity and adhesion properties are maintained even after the structure has been stored for a period of time. Accordingly, the present invention offers a hygienic product having a well defined and controlled course of wetting.

A fibrous structure in accordance with the invention is primarily distinguished by one or several types of polar silicon-containing compounds, being bound to at least one portion of the surface of the fibrous structure by interaction between the surface and the silicon-containing compounds.

As previously mentioned, the fibrous structure according to the invention exhibits a predetermined degree of hydrophilicity and adhesion properties which are substantially unaffected by wetting of the fibrous structure.

In accordance with one embodiment, the silicon-containing compound consists of a compound of the type $SiO_xH_y$ wherein x preferably is in the range of 1 to 4, and y preferably in the range of 0 to 4.

An advantage with a fibrous structure of this type is that the wetting characteristics of the structure has proved to be substantially constant during wetting and that the fibrous structure is comparatively resistant to ageing.

Without being in anyway limited by the following theoretical explanation of why a hydrophilic surface having polar silicon-containing compounds exhibits a stable hydrophilicity and adhesion properties both after repeated wetting and after ageing of the material structure, one could think that the polar silicon-containing compounds form a kind of clusters which are sufficiently large to inhibit reorientation of polymer chains and, accordingly, the ageing phenomenon. However, the theory is not fully developed and should accordingly not be regarded as being binding to the invention.

As already mentioned, the fibrous structures in accordance with the invention exhibit at least one polar silicon-containing material surface, or portion of a surface. However, it is possible according to the invention to apply silicon-containing compounds to both surfaces of a sheet of material. Further, one or both surfaces of the material may exhibit one or more delimited areas having polar silicon-containing compounds.

According to one aspect of the invention, the fibrous structure comprises one or more non-woven materials.

According to one further aspect of the invention, the fibrous structure of the invention may, for instance, be used as fluid permeable cover sheet for absorbent articles or as a fluid transfer layer between the fluid permeable cover sheet and the absorbent structure in an absorbent article, or for the absorbent structure itself.

According to another aspect of the invention, the fibrous structure of the invention may be used as a liquid absorbing wipe, or as a component in a wipe or the like.

In still another aspect of the invention, the fibrous structure may comprise one or more tissue layers.

As well known to the man skilled in the art, the term "tissue" commonly covers fibrous material based on cellulose or cellulose in combination with synthetic fibres and typically used in the manufacture of household items such as kitchen towels, toilet paper, or napkins, in the manufacture of industrial wipes for absorption of different liquids, or else for the manufacture of layers entering the structure of absorbent articles such as diapers, incontinence guards, sanitary napkins or the like.

The invention additionally concerns an absorbent article such as a diaper, an incontinence guard, a sanitary napkin or the like comprising an absorption body being enclosed between a fluid impermeable cover layer and a fluid permeable cover layer, said article comprising at least one portion comprising a fibrous structure in accordance with the invention.

The fibrous structure may constitute a part or all of the fluid pervious cover layer and/or of a fluid transfer layer positioned between the fluid pervious cover layer and the absorption body.

In a hygienic product for fluid absorption purposes and being made of a plurality of individual layers, fluid transfer between the different layers is of great importance both for the rate of wicking within each individual layer and for the total fluid uptake capacity of the hygienic product. From the above discussion it appears that in fluid absorbent articles of this kind it is very important that all layers of material exhibit a well-defined and stable degree of hydrophilicity which only varies to a very limited extent with wetting and ageing.

According to one of the aspects of the invention, the liquid permeable cover sheet, the fluid transfer layer, and the absorption body have different degrees of hydrophilicity.

According to one of the preferred embodiments of the invention, the fluid transfer layer of the hygiene article comprises a set of several fibrous structures according to the invention, the set of fibrous structures presenting a gradient of degrees of hydrophilicity.

The invention further concerns a hygienic product such as a wipe, a wound dressing or the like, comprising a fibrous structure in accordance with the invention.

The invention further concerns a method for producing a fibrous structure having one or more types of polar silicon-containing compounds bound to at least a portion of a surface of the fibrous structure. The method is primarily distinguished by the fact that the fibrous structure is submitted to an atmosphere comprising excited and unstable species, as-obtained through the application of an electrical discharge to an initial mixture comprising a carrier gas, an oxidant, and at least one type of silicon-containing gaseous compound.

An advantage with a method of this kind, is that it is carried out under dry conditions which implies that the silicon-containing compound does not have to be solved in a solvent before application which means that the method is advantageous from an environmental point of view.

In accordance with a preferred embodiment, the treatment is based on an electrical discharge led in a gaseous mixture, leading to the formation of a plasma.

As well known, a plasma is a gaseous medium containing ions, radicals, electrons, excited and unstable species. It can be obtained through supplying to a gaseous mixture a sufficient amount of energy, at a defined pressure, for example very low pressure or atmospheric pressure.

All the species of the plasma can react between them and/or with the components of the gaseous mixture to create new ions, radicals, and excited species.

When it is carried out at atmospheric pressure with a high voltage electrical signal as energy supply, the plasma is commonly called "corona".

According to this preferred embodiment, the fibrous structure is therefore submitted to an electrical discharge, in presence of a gaseous mixture comprising at least one type of silicon-containing gaseous compound, oxygen or other oxygen-containing gas, and a carrier gas.

According to another embodiment of the invention, the fibrous structure is submitted to a treatment atmosphere as-obtained in post-discharge of an electrical discharge applied to a gaseous mixture comprising at least one type of silicon-containing gaseous compound, oxygen or other oxygen-containing gas, and a carrier gas (the fibrous structure is here submitted to the treatment atmosphere outside the discharge).

In any case, the unstable and excited species of the atmosphere react with the polymer chains of the surface of the fibrous structure, leading to the formation of radicals of said polymer chains. These radicals can then react with the species present in their vicinity forming this way new bondings and new functional groups on the surface. Functional groups which are relevant to the present invention are polar silicon-containing groups. The functional groups this way introduced on the surface of the material are much more strongly bound to the surface than an active substance which has been applied as a conventional coating.

A method for corona treatment is described in U.S. Pat. No. 5,576,076, U.S. Pat. No. 5,527,629 and U.S. Pat. No. 5,523,124. The gas mixture is based on a carrier gas which usually is nitrogen, a silicon-containing compound and an oxidant. The treatment creates a layer of material having a glassy, hydrophilic surface.

The disclosed method is suitable for use in connection with the invention. However, the invention is not limited to the method described in the above entioned applications, but comprises all types of gas phase treatments in which polar silicon-containing groups are introduced to a surface of a fibrous structure.

In accordance with a preferred embodiment the silicon-containing compound in the gas mixture is a silane compound. Some examples of such compounds are $Si_nH_{n+2}$ where n preferably is from 1 to 4, silicon hydroxide, halogenated silanes, alkoxysilane or organosilane. The oxidant is preferably oxygen or other oxygen-containing gases such as, for instance, CO, CO, NO, $N_2O$ or $NO_2$. The carrier gas may consist of nitrogen, argon, helium, or a mixture thereof.

According to one of the embodiments of the invention, prior to being treated with the medium comprising unstable and excited species, resulting from the application of an electrical discharge to the gaseous mixture comprising the silicon-containing gaseous compound, an oxidant and a carrier gas, the fibrous structure has been in a first step submitted to a corona discharge under air (surface preparation).

BRIEF DESCRIPTION OF THE DRAWINGS

Other characteristics and advantages of the present invention will become apparent from the following detailed description of preferred embodiments thereof in connection with the appended drawings in which.

DETAILED DESCRIPTION OF THE PREFERRED EMBODIMENTS

Figure 1:
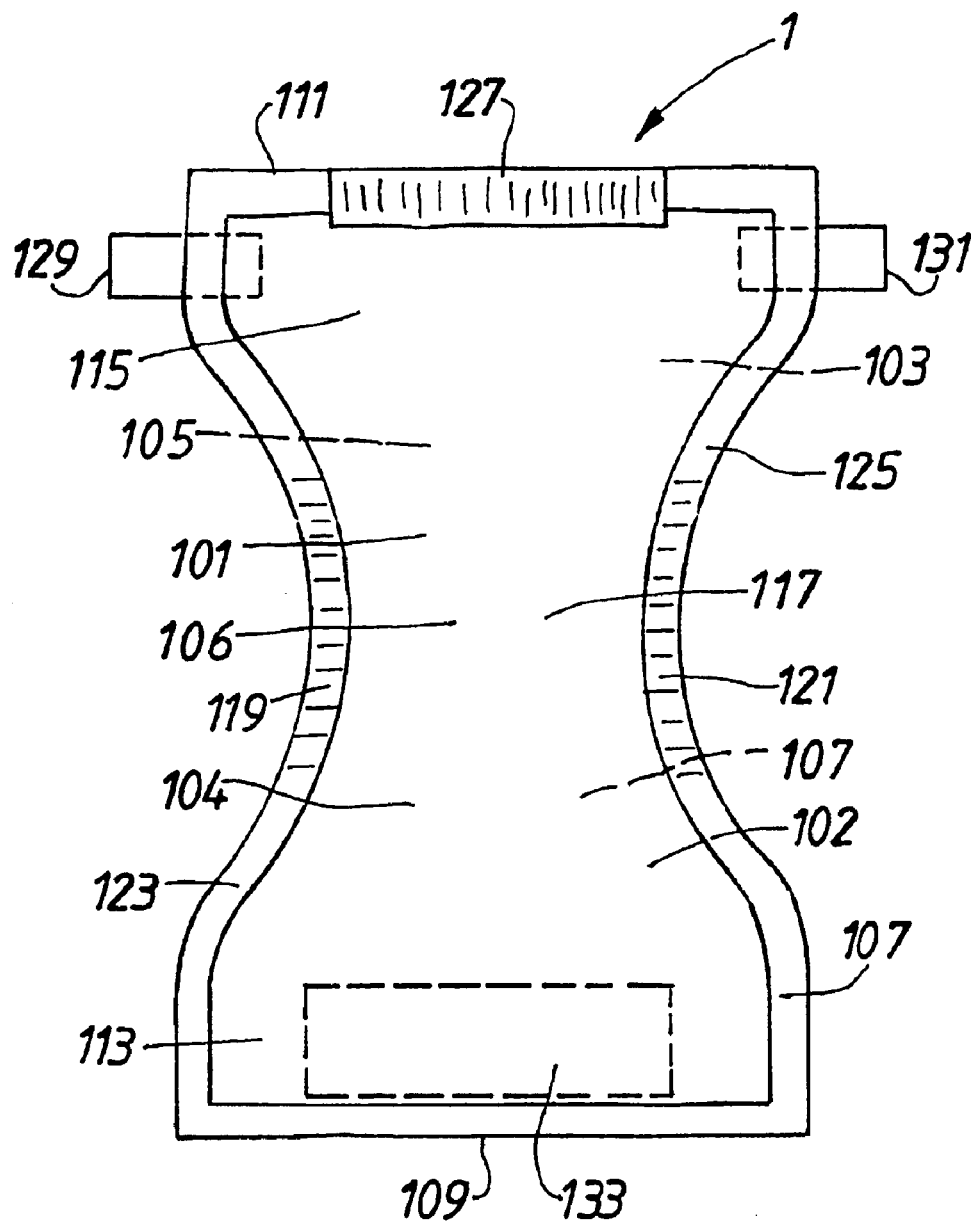
FIG. 1 shows a diaper seen from the side which is intended to be facing a user during use.

The diaper 100 which is shown in FIG. 1 comprises a fluid permeable cover sheet 101, a fluid impermeable cover sheet 103 and an absorption body 105 enclosed between the cover sheets 101, 103. The fluid impermeable cover sheet 103 may consist of a fluid impermeable plastic film, a sheet of non-woven material which has been provided with a fluid resistant coating or any other type of flexible sheet material which resists fluid penetration. Generally, it is an advantage if the fluid impermeable cover sheet 103 is breathable at least to some extent, implying that water vapor may pass through the cover sheet.

The covering sheets 101,103 have a planar extension which is somewhat greater than the planar extension of the absorption body 105 and comprise edge portions 107 which protrude beyond the peripheral edge of the absorption body 105. The cover sheets 101,103 are joined within the protruding edge portions 107 by means of, for instance, adhesive or welding with heat or ultrasonically.

Further, the diaper 100 has two longitudinally extending side edges 123,125, a front end edge 109 and a rear end edge 111, and exhibits a front portion 113, a rear portion 115, and an intermediate crotch portion 117 which is narrower than the end portions 113,115.

In addition, elements 119,121 are arranged along the side edges 123,125 at the crotch portion 117 of the diaper. The purpose of the elastic elements 119,121 is to provide a means for keeping the diaper in sealing contact around the legs of a user when the diaper is being worn. An additional elastic element 127 is arranged along the rear end edge 111 and is provided in order to give the diaper 100 a certain degree of extensibility and conformability and to act as a sealing means against waist leakage.

A tape tab 129,131 is arranged at each side edge 123,125 close to the rear end edge 111. The tape tabs 129,131 constitute fastening means for the diaper 100 and permit the diaper 100 to be formed into a garment enclosing the lower part of the wearer's body in a manner similar to that of a pair of underpants. The tape tabs 129,131 cooperate with a receiving area 133 arranged on the fluid impermeable cover sheet 103 at the front portion 113 of the diaper. The receiving area 133 may be constituted by a reinforcing material which has been laminated to the fluid impermeable cover sheet 103. By reinforcing the cover sheet the diaper 100 may be closed and reopened without affecting the adhesive properties of tape tabs 129,131 or causing the fluid impermeable cover sheet 103 to rupture.

It is, of course, possible to use any of a number of different alternative types of fastening elements. Some examples of such alternative fastening elements are hook and-loop surfaces, press studs, tying ribbons, or similar.

The absorption body 105 usually comprises one or more layers of cellulose fibres, such as fluffed cellulose pulp.

In addition to cellulosic fibres the absorption body 105 may comprise superabsorbent material which is a material in the form of fibres, particles, granules, film or the like and which has the ability to absorb fluid in an amount corresponding to several times the weight of the superabsorbent material itself. Superabsorbent materials bind the absorbed liquid and form a liquid-containing gel.

The absorption body 105 may further comprise a binding agent, shape stabilizing means, or the like. It is also possible to use additional absorbent layers in order to improve the absorption properties, such as different types of liquid dispersing inserts or material layers.

The absorption body 105 may be chemically or mechanically treated in order to change the absorption characteristics.

A commonly employed way of improving the wicking ability of an absorbent structure is to provide the absorption body with a pattern of compressed areas. Furthermore, it is possible to use absorbent materials such as absorbent non-woven materials, absorbent foams, or the like. Likewise, all conceivable combinations of suitable absorbent materials may be used.

The fluid permeable cover layer 101 comprises one or more layers of material wherein at least one layer of material consists of a fibrous structure in accordance with the invention.

A fibrous structure in accordance with the invention can enter the structure of an upper layer 106 which during use of the diaper 100 will be in contact with the body of the user and/or of a lower fluid transfer layer 108 which is situated between the upper, skin-contacting layer 106 and the absorption body 105 which is arranged beneath the fluid permeable cover layer 101 and/or of the absorption body 105. In case of both the upper, skin-contacting layer 106, the absorption body, and the fluid transfer layer 108 being fibrous structures in accordance with the invention it is advantageous if those layers exhibit mutually different degrees of hydrophilicity. This may, for instance, be achieved by using gas mixtures of different composition when treating the different fibrous structures.

The invention is not restricted to any particular type of material. Accordingly, the choice of polymer, fibre thickness or density of fibres is dependent on the type of article (for example absorbent article) for which the fibrous structure is intended as well as the function and location of the fibrous structure in the article (searching for hydrophilicity properties or else for example for adhesion properties).

By way of illustration, fibrous structures are commonly made of polypropylene, polyethylene, polyester, and their co-polymers. However, the invention should not be restricted to these polymers.

One example of another type of useful polymers are biodegradable polymers. In order for biodegradable materials to perform well as a fluid pervious cover sheet it is usually necessary to treat the material with a hydrophilic agent or to perforate the material. As has been previously mentioned, the usual way of accomplishing wettability in a fibrous sheet material is by coating the material with surfactants which are less environmentally friendly than desired. Accordingly, the present invention provides a means for creating a fluid permeable cover sheet having environmentally beneficial properties both with respect to biodegradability and because the use of surfactants can be avoided.

Examples of fibrous structures according to the invention are hereafter described.

EXAMPLE 1

ESCA Measurements

In order to examine the chemical composition of the surface of a material the chemical analysis was performed by electron spectroscopy, ESCA. In ESCA the material surface is irradiated with X-rays. The high energy X-rays result in electrons being emitted from the surface of the material.

The binding energy of an emitted electron is obtained from:

$$E_b = h\nu - E_k$$

$E_b$ = the binding energy of the electron
$E_k$ = the kinetic energy of the electron
$h\nu$ = the radiation energy.

The energy of the X-rays is known and the kinetic energy is obtained by measuring the velocity of the electron. Accordingly a value for the binding energy of the emitted electron may be obtained which implies that the chemical composition of the surface can be identified.

Samples of Example 1
1a. Untreated polypropylene non-woven material.
2a. Polypropylene non-woven material which has been corona treated according to the invention to introduce polar silicon-containing groups on the surface of the material.
2b. Polypropylene non-woven material which has been washed after having been corona treated.

The operating conditions under which the samples 2a and 2b were treated according to the invention are as follows:

Speed of the web=26 m/min.
Width of the web=0.65 m
Electrical power of corona=1690 W
Flow rate of $N_2$=94 l/min.
Flow rate of $N_2O$=0.39 l/min.
Flow rate of $SiH_4$=0.115 l/min.

The web was here treated in two steps: in a first step, corona treated under air, and in a second step, corona treated with injection of the here above described gaseous mixture.

When the material is washed, this is done by being submerged in a container with distilled water. The temperature of the distilled water is 37° C. The material is left in the water for 15 seconds and is hereafter removed from the water and laid out flat to dry.

Results of example 1—Concentration of oxygen and silicon (%) on the surface of the material

| Sample | 1 | 2a | 2b |
|--------|-----|------|------|
| O      | 0.7 | 31.9 | 35.2 |
| Si     | —   | 9.2  | 11.2 |

The results show that the corona-treated non-woven material according to the invention exhibits an oxygen concentration which is 31.9% and a silicon concentration which is 9.2% on the surface of the material. The oxygen and silicon concentrations are maintained even after washing of the material as is evident from sample 2b.

EXAMPLE 2

Using a Set of Cahn Scales to Determine the Fibre Contact Angle.

Figure 2:
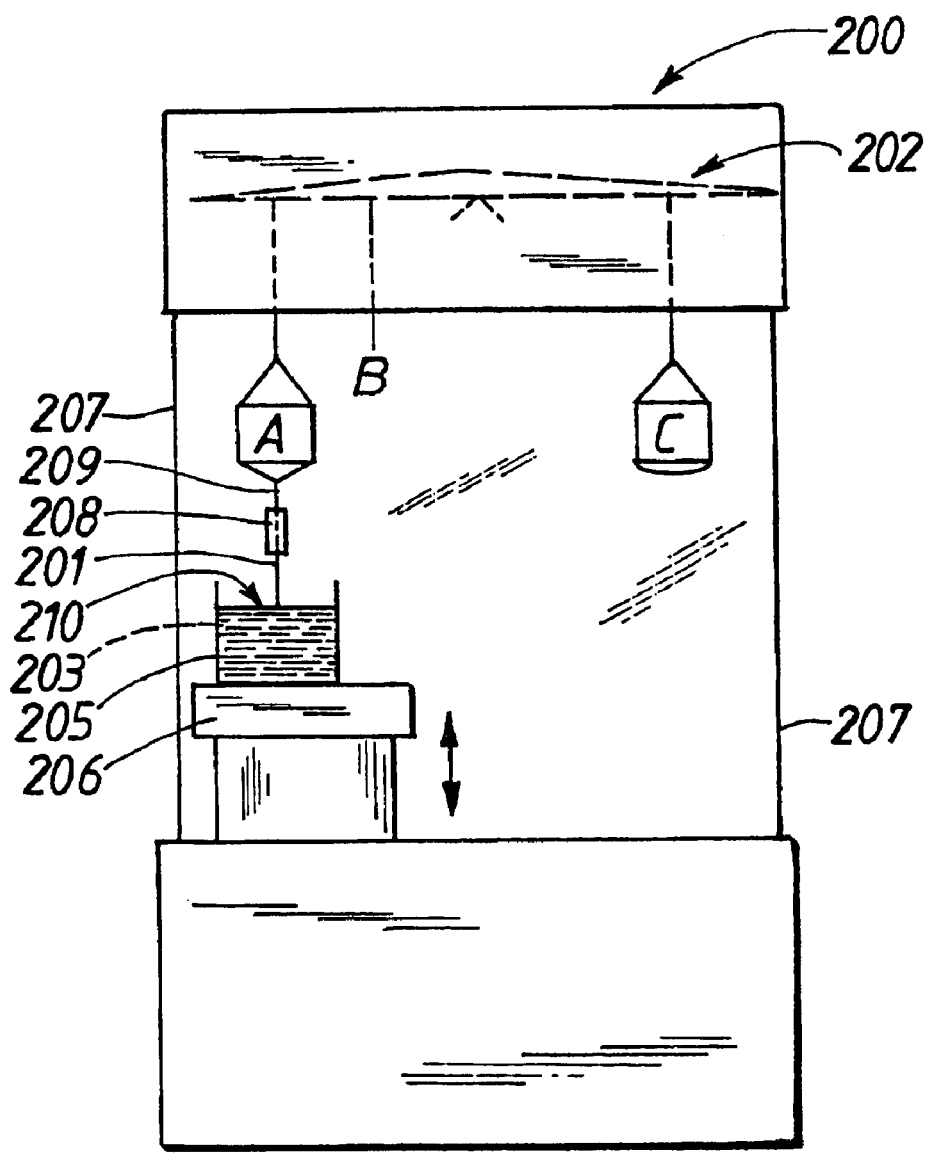
FIG. 2 shows an instrument for measuring the contact angle for individual fibers.

Wilhelmy's method was used to determine the fibre wetting angle. The measurement was performed using a set of Cahn scales 200, which is shown in FIG. 2. During the measuring interval a fibre 201 is vertically suspended in an extremely sensitive set of beam scales 202. A liquid container 205 is placed on a movable table 206 directly beneath the fibre 201. When the fibre 201 is immersed in the liquid 203 a liquid meniscus is formed around the fibre, affecting the fibre 201 with a vertical force.

The force which arises between the liquid 203 and the fibre 201 can be either positive or negative, depending on the surface characteristics of the fibre and the liquid. An attraction force which is a positive force will arise when the contact angle between the fibre and the liquid is less than 90°. When the system has a contact angle which is greater than 90° the liquid and the fibre will repel each other which implies force. The attraction or repelling force is determined by means of the set of beam scales. The force is related to the contact angle in accordance with:

$$F = \gamma_L p \cos\theta + mg - \rho_L lgA$$

F=registered force (N)
$\gamma_L$=liquid surface energy (J/m²)
p fibre circumference (m)
θ=contact angle in the interface fibre-liquid-air (°)
m mass of mounted fibre (kg)
g gravitational constant (m/s²)
$\rho_L$=liquid density (kg/m³)
l=wet fibre length (m)

A=cross-sectional fibre area (m²).

The second term in the equation represents the weight of the mounted fibre. The third term is what is known as the buoyancy-force, which is the weight loss which arises as a result of the volume of liquid which is pushed aside. In a computer (not shown) and equipped with a calculation program for determination of contact angles these two parameters are usually being compensated for which simplifies the equation into:

$$F = \gamma_L p \cos \theta$$

The advancing contact angle and the receding contact angle specify if the dynamic contact angle is measured when a liquid is advancing over a dry surface or when a liquid is receding from a wet surface. Accordingly, the value for the advancing contact angle is obtained when the fibre is lowered into the liquid and the value for the receding contact angle is obtained when the fibre is withdrawn from the liquid.

The set of beam scales 202 has three pans (see FIG. 2). A first pan A has an accuracy of $10^{-6}$, which makes it suitable for measuring contact angles for fibres. However, the set of scales may also be used to determine surface energy for liquids wherein a less sensitive, second pan B is used. The set of scales is tared by placing balancing weights in a third pan C.

In order to avoid that air draught, dust or the like will interfere with the measurement the pans and the moveable table 206 are protected by slidable glass screens 207. In addition, the screens make it possible to control air humidity and temperature. In order to avoid disturbing vibrations during the course of the measurement the set of scales is placed on a foundation (not shown).

The table on which the liquid container 205 is placed can be raised and lowered by means of an engine. The speed of the table 206 is controlled by the computer and is specified before the start of a measurement. Other parameters which are fed into the computer before starting the measurement is the surface energy of the liquid and the circumference of the fibre 210.

Before starting the measurement, a fibre 201 is mounted on a piece of tape 208 with a part of the fibre being free from the tape. The mounted fibre 201 is gripped by a metal clip 209 and is suspended from the first pan A. The set of scales 202 has before then been tared with only the metal clip 209 being suspended from the first pan A. A test liquid 203 having known surface energy is placed in the liquid container 205 on the table 206 below the fibre 201.

The fibre 201 should hang perpendicularly to the surface of the liquid 210 and must be absolutely still, the set of scales showing a stable value, before the measurement is started.

When a measurement is started the computer registers a base line whereafter the table 206 is raised. When one or a few millimeters of the fibre 201 has been dipped into the liquid 203 the computer is ordered to stop the table.

Subsequently, the table 206 is lowered. During the course of the test the variation of the force along the fibre is shown on the screen of the computer. When the measurement is completed representative portions is selected from the advancing and the receding curves, respectively. Next, the computer calculates the contact angles employing Wilhelmy's equation.

Contact angle measurements were performed on single fibres taken from a 18 g/m² nonwoven material consisting of polypropylene. The fibres were dipped into a liquid container with distilled water.

Samples of Example 2

1a. polypropylene fibres from an untreated nonwoven material;

1c. after storage of the untreated non-woven material of 1a. for three months;

2a. polypropylene fibres from a non-woven material which has been corona treated according to the invention in order to introduce polar, silicon-containing groups to the surface of the material;

2b. after washing of the corona treated non-woven material in 2a;

2c. after storage of the corona treated non-woven material in 2a for five weeks (no washing);

2d. after washing and subsequent storage of the corona treated non-woven material in 2a for five weeks.

The operating conditions under which the samples 2a, 2b, 2c and 2d were treated according to the invention are as follows:

Speed of the web=26 m/min

Width of the web=0.65 m

Electrical power of corona=1690 W

Flow rate of $N_2$=94 l/min

Flow rate of $N_2O$=0.39 l/min

Flow rate of $SiH_4$=0.115 l/min.

The web was, in a first step, corona treated under air and in a second step, corona treated with injection of the here above described gaseous mixture.

When the material is washed, this is done by being placed in a container with distilled water. The temperature of the distilled water is 37° C. The material is left in the water for 15 seconds and is thereafter removed from the water and laid out flat to dry. The contact angle is measured for individual fibres from the washed nonwoven material.

| results of example 2 | |
|---|---|
| Sample | Contact angle (Advancing/Receding) |
| 1a | 99/93° |
| 1c | 98/90° |
| 2a | 50/25° |
| 2b | 58/31° |
| 2c | 50/19° |
| 2d | 52/23° |

The results show that untreated polypropylene fibres have a contact angle which is over 90', implying that such fibres are hydrophobic. Polypropylene fibres from a non-woven material which has been corona treated according to the invention to introduce polar silicon-containing groups to the surface of the material do on the other hand, exhibit a considerably lower contact angle as is shown by the results for samples 2a–d. After washing of the corona treated nonwoven material the contact angle has been changed from 50° to 58° for the advancing angle and from 25° to 31° for the receding angle which implies that the degree of hydrophilicity is maintained at a relatively constant level after washing of the material.

Sample 2c concerns fibres from the corona treated nonwoven material which has been stored for five weeks after the first measurement and the second measurement as performed in order to determine the effect of ageing on the material.

The advancing angle was found to be 50° both for the fibres of the stored nonwoven material and for the fibres from the non-woven material which had not been stored.

The receding angle was found to be 25° for the unstored material and 19° for the material which had been stored which implies that the degree of hydrophilicity was substantially unaffected after a five weeks storage.

Finally, sample 2d concerns polypropylene fibres from a corona treated nonwoven material which was washed and then stored for five weeks. The degree of hydrophilicity of sample 2d is almost constant as compared to the unstored and unwashed sample 2a which indicates that the introduced polar silicon-containing groups are stably bound to the fibrous surface.

EXAMPLE 3

Determination of Liquid Penetration Time for a Sheet of Material

In order to determine the liquid penetration time for the fibrous structure, the EDANA test method no. 14-20-06 W25 used. The method measures the time which is required for a predetermined amount of liquid to pass through a topsheet of nonwoven material wherein the nonwoven material is in contact with a standard absorbent material arranged beneath the nonwoven material.

The standard absorbent material consists of 5 layers of filter paper, ERT FF3 100×100 mm. When performing the measurement the filter papers are placed on a base plate of plexiglass. A non woven sample is placed on top of the filter papers with the side which is intended to be facing the skin of a user facing upwards. A strike-through plate of the brand LISTER from Lenzing AG is placed on top of the sample, taking care that the strike-through plate is well centred. An instrument for measuring penetration time is placed above the strike-through plate with the distance between the liquid exit pipe on the instrument for measuring penetration time and the strike-through plate being 30 mm.
5.0 ml test liquid is measured and poured into the liquid container on the instrument, thereafter the measurement is started. The instrument for measuring penetration time is of the same brand as the strike-through plate.

The measurement was performed on a nonwoven material consisting of polypropylene and having a basis weight of 18 g/m². The test liquid was a 0.9% NaCl-solution.

Samples of Example 3

1a. untreated polypropylene non-woven material;

2a. polypropylene nonwoven material which has been corona treated according to the invention in order to introduce polar silicon containing groups to the surface of the material;

2b. after washing of the corona treated nonwoven material of 2a.

The operating conditions under which the samples 2a and 2b were treated are as follows Speed of the web=26 m/min Width of the web=0.65 m Electrical power of corona=1690 W Flow rate of $N_2$=94 l/min Flow rate of $N_2O$=0.39 l/min.

Flow rate of $SiH_4$=0.115 l/min.

The web was, in a first step, corona treated under air and in a second step, corona treated with injection of the here above described gaseous mixture.

The material is washed by being placed in a container with distilled water. The distilled water has a temperature of 37° C. The material is left in the water for 15 seconds and is subsequently removed from the water and laid out flat to dry.

| Results of example 3 | |
|---|---|
| Sample | Time (seconds) |
| 1 | >300 |
| 2a | 2.7 |
| 2b | 2.9 |

The results show that the untreated nonwoven material 1a exhibits a penetration time which is over 300 seconds which implies that the liquid does not penetrate through the nonwoven material during the period of measuring which is 300 seconds (5 minutes). The nonwoven material of sample 2b which has been corona treated according to the invention to introduced polar silicon containing groups to the surface of the material exhibits a penetration time which is 2.9 seconds which is almost equal to the penetration time for the unwashed corona treated nonwoven material.

The invention shall not be regarded as being restricted to the embodiments which have been described herein. Accordingly, a plurality of further variants and modifications are conceivable within the scope of the appended claims.

Therefore, if the invention and all its advantages have been particularly described and illustrated in the case of non-woven fibrous structures used in the baby diaper field, as will be clearly apparent to the man skilled in the art, the invention finds a much larger field of application, including for example woven fibrous structures, of either the natural or synthetic type.

Besides the hygienic field, many other fields of application can be envisaged within the scope of the present invention, with in each case different kinds of properties that can be looked for and reached according to the invention (hydrophilicity, adhesion, anti-stain treatment . . . ).

Some of those hundreds of uses have been illustrated at the beginning of the present description.

What is claimed is:

1. An absorbent article comprising:
an absorbent body enclosed between a fluid impermeable cover sheet and a fluid permeable cover sheet wherein the fluid permeable cover sheet comprises at least one fibrous structure and wherein:
a) at least a portion of a surface of at least one of said fibrous structures is bound to at least one polar, silicon containing compound by interaction between the surface and the silicon-containing compound; and
b) the fibrous structure(s) exhibit(s) a predetermined degree of hydrophilicity which is substantially unaffected by wetting of the structure, and/or exhibit(s) adhesion properties which are substantially unaffected by wetting of the structure, wherein said fibrous structure(s) bound to a silicon containing compound has been submitted to an electrical discharge, in the presence of a gaseous mixture comprising at least one type of silicon-containing gaseous compound, oxygen or oxygen-containing gas, and a carrier gas.

2. An absorbent article according to claim 1, wherein the silicon containing compound is a compound of the type $SiO_xH_y$, wherein x is in the range of 1 to 4, and y in the range of 0 to 4.

3. An absorbent article according to claim 2, characterized in that at least one of said fibrous structures comprises one or more tissue sheets.

4. An absorbent article according to claim 2, characterized in that at least one of the fibrous structures comprises one or more non-woven materials.

5. An absorbent article according to claim 2, characterized in that said fibrous structure(s) bound to a silicon containing compound has been submitted to a treatment atmosphere as-obtained in post-discharge of an electrical discharge applied to a gaseous mixture comprising at least one type of silicon-containing gaseous compound, oxygen or other oxygen-containing gas, and a carrier gas.

6. An absorbent article according to claim 2, wherein it is a diaper, a sanitary napkin, or an incontinence guard.

7. An absorbent article according to claim 2, wherein it is an hygienic article comprising a wipe or a wound dressing.

8. An absorbent article according to claim 1, characterized in that at least one of said fibrous structures comprises one or more tissue sheets.

9. An absorbent article according to claim 8, characterized in that said fibrous structure(s) bound to a silicon containing compound has been submitted to a treatment atmosphere as-obtained in post-discharge of an electrical discharge applied to a gaseous mixture comprising at least one type of silicon-containing gaseous compound, oxygen or other oxygen-containing gas, and a carrier gas.

10. An absorbent article according to claim 8, wherein it is a diaper, a sanitary napkin, or an incontinence guard.

11. An absorbent article according to claim 8, wherein it is an hygienic article comprising a wipe or a wound dressing.

12. An absorbent article according to claim 1, characterized in that at least one of the fibrous structures comprises one or more non-woven materials.

13. An absorbent article according to claim 12, characterized in that said fibrous structure(s) bound to a silicon containing compound has been submitted to a treatment atmosphere as-obtained in post-discharge of an electrical discharge applied to a gaseous mixture comprising at least one type of silicon-containing gaseous compound, oxygen or other oxygen-containing gas, and a carrier gas.

14. An absorbent article according to claim 12, wherein it is a diaper, a sanitary napkin, or an incontinence guard.

15. An absorbent article according to claim 12, wherein it is an hygienic article comprising a wipe or a wound dressing.

16. An absorbent article according to claim 1, characterized in that said fibrous structure(s) bound to a silicon containing compound has been submitted to a treatment atmosphere as-obtained in post-discharge of an electrical discharge applied to a gaseous mixture comprising at least one type of silicon-containing gaseous compound, oxygen or other oxygen-containing gas, and a carrier gas.

17. An absorbent article according to claim 16, characterized in that said fibrous structure(s) bound to a silicon containing compound, prior to being submitted to said electrical discharge, in presence of said gaseous mixture, or to said treatment atmosphere in post-discharge, has been in a first step submitted to a corona discharge under air.

18. An absorbent article according to claim 16, wherein it is a diaper, a sanitary napkin, or an incontinence guard.

19. An absorbent article according to claim 1, wherein said fibrous structure(s) bound to a silicon containing compound, prior to being submitted to said electrical discharge in the presence of said gaseous mixture, or to said treatment atmosphere in post-discharge, has been in a first step submitted to a corona discharge under air.

20. An absorbent article according to claim 19, wherein it is a diaper, a sanitary napkin, or an incontinence guard.

21. An absorbent article according to claim 19, wherein it is an hygienic article comprising a wipe or a wound dressing.

22. An absorbent article according to claim 1, wherein it is a diaper, a sanitary napkin, or an incontinence guard.

23. An absorbent article according to claim 22, characterized in that the liquid permeable cover sheet comprises one or more of said fibrous structures bound to a silicon containing compound.

24. An absorbent article according to claim 23, characterized in that a fluid transfer layer is arranged between the liquid permeable cover sheet and the absorption body, wherein the fluid transfer layer comprises one or more of said fibrous structures bound to a silicon containing compound.

25. An absorbent article according to claim 22, characterized in that a fluid transfer layer is arranged between the liquid permeable cover sheet and the absorption body, wherein the fluid transfer layer comprises one or more of said fibrous structures bound to a silicon containing compound.

26. An absorbent article according to claim 25, characterized in that said liquid permeable cover sheet, said fluid transfer layer, and said absorption body have different degrees of hydrophilicity.

27. An absorbent article according to claim 26, characterized in that said fluid transfer layer comprises a set of several of said fibrous structures bound to a silicon containing compound, and in that said set of fibrous structures presents a gradient of degrees of hydrophilicity.

28. An absorbent article according to claim 25, characterized in that said fluid transfer layer comprises a set of several of said fibrous structures bound to a silicon containing compound, and in that said set of fibrous structures presents a gradient of degrees of hydrophilicity.

29. An absorbent article according to claim 1, wherein it is an hygienic article comprising a wipe or a wound dressing.

30. An absorbent article according to claim 29, characterized in that it comprises a set of several of said fibrous structures bound to a silicon containing compound, and in that said set of fibrous structures presents a gradient of degrees of hydrophilicity.

31. The absorbent article according to claim 1, wherein the fluid impermeable cover sheet is breathable.

32. The absorbent article according to claim 1, wherein the fluid impermeable cover sheet is laminated to a reinforcing material.

33. The absorbent article according to claim 1, wherein the absorbent body contains cellulosic fibers.

34. The absorbent article according to claim 1, wherein the absorbent body contains a superabsorbent material.

35. The absorbent article according to claim 1, wherein the fibrous structure comprises a non-woven derived from polypropylene.

* * * * *